United States Patent [19]

McConnachie et al.

[11] Patent Number: 5,906,968
[45] Date of Patent: *May 25, 1999

[54] METHOD OF SYNTHESIZING $MO_3S_X$ CONTAINING COMPOUNDS

[75] Inventors: Jonathan M. McConnachie, Flemington; Edward I. Stiefel, Bridgewater, both of N.J.; Ian Alexander Weston Bell, Abingdon; Velautha-Cumaran Arunasalam, Greenford, both of United Kingdom

[73] Assignee: Exxon Research & Engineering Company, Florham Park, N.J.

[*] Notice: This patent is subject to a terminal disclaimer.

[21] Appl. No.: 08/990,053

[22] Filed: Dec. 12, 1997

[51] Int. Cl.[6] .......................... C10M 139/00; C07F 11/00
[52] U.S. Cl. .................. 508/363; 556/38; 556/57
[58] Field of Search ................ 508/363; 556/38, 556/57

[56] References Cited

U.S. PATENT DOCUMENTS 5,631,213  5/1997  Tanaka et al. ........................ 508/363
5,688,748  11/1997  Tomizawa .............................. 508/363

OTHER PUBLICATIONS

Shibahara, "Synthesis of Sulphur–Bridged Molybdenum and Tungsten Coordination Compounds," Coordination Chemistry Reviews, 123 (1993), 73–147.

Primary Examiner—Jerry D. Johnson
Attorney, Agent, or Firm—Ohlandt, Greeley, Ruggiero & Perle

[57] ABSTRACT

A method of making an oil-soluble or oil-dispersible trinuclear molybdenum-sulfur compound, comprising: reacting two to less than three equivalents of a tetrahydrocarbyl thiuram disulfide and one equivalent of a compound containing the $[Mo_3S_{13}]^{2-}$ ion to produce a trinuclear molybdenum compound of the formula $Mo_3S_x(L)_4$ wherein x is from 4 to 10 and L is dihydrocarbyl-dithiocarbamate.

11 Claims, No Drawings

METHOD OF SYNTHESIZING $MO_3S_X$ CONTAINING COMPOUNDS

FIELD OF THE INVENTION

The invention relates to a method for synthesizing certain trinuclear molybdenum sulfur compounds.

BACKGROUND OF THE INVENTION

There is a continuing need for new lubricant additives that possess antifriction, antiwear and antioxidant properties. Some molybdenum compounds possess one or more of these properties but are typically less commercially attractive to produce in comparison to other antifriction, antiwear and antioxidant additives. Trinuclear molybdenum sulfur complexes have been found to be promising lube oil additives. Thus, new methods for synthesizing trinuclear molybdenum sulfur containing lube additives would be desirable. Applicants' invention addresses these needs.

SUMMARY OF THE INVENTION

The present invention provides for:

a method of making an oil-soluble or oil-dispersible trinuclear molybdenum-sulfur compound, comprising: reacting two to less than three equivalents of a tetrahydrocarbyl thiuram disulfide and one equivalent of a compound containing the $[Mo_3S_{13}]^{2-}$ ion to produce a trinuclear molybdenum compound of the formula $Mo_3S_x(L)_4$ wherein x is from 4 to 10 and L is dihydrocarbyl-dithiocarbamate.

The present invention also provides for the reaction products produced by the disclosed processes.

The present invention may suitably comprise, consist, or consist essentially of the elements described herein.

DETAILED DESCRIPTION OF THE INVENTION

The present invention provides for a process for synthesizing trinuclear molybdenum $Mo_3S_x$ core-containing compounds. Therein x is from 4 to 10, preferably 7 and mixtures thereof. More preferably the reaction product substantially comprises oil-soluble or oil-dispersible $Mo_3S_7$ core containing compounds. In these compounds the core is associated with suitable ligands, $L_y$, wherein y is of a sufficient number, type and charge to render the compound oil soluble and to neutralize the charge on the $Mo_3S_x$ core. Thus, the reaction product is represented by the formula $Mo_3S_xL_y$. The ligands are dihydrocarbyl dithiocarbamate ligands ($-S_2CNR_2$). The dihydrocarbyl groups, $R_2$, should be suitable to impart oil solubility.

The term "hydrocarbyl" denotes a substituent having carbon atoms directly attached to the remainder of the ligand and is predominantly hydrocarbyl in character within the context of this invention. Such substituents include the following: (1) hydrocarbon substituents, that is, aliphatic (for example alkyl or alkenyl), alicyclic (for example cycloalkyl or cycloalkenyl) substituents, aromatic-, aliphatic- and alicyclic-substituted aromatic nuclei and the like, as well as cyclic subsituents wherein the ring is completed through another portion or the ligand (that is, any two indicated substituents may together form an alicyclic group); (2) substitued hydrocarbon substituents, that is, those containing nonhydrocarbon groups which, in the context of this invention, do not alter the predominantly hydrocarbyl character of the substituent. Those skilled in the art will be aware of suitable groups (e.g., halo, (especially chloro and fluoro), amino, alkoxyl, mercapto, alkylmercapto, nitro, nitroso, sulfoxy, etc.); (3) hetero substituents, that is, substituents which, while predominantly hydrocarbon in character within the context of this invention, contain atoms other than carbon present in a chain or ring otherwise composed of carbon atoms.

The hydrocarbyl groups are preferably alkyl (e.g., in which the carbon atom attached to the remainder of the ligand is primary, secondary or tertiary), aryl, substituted aryl and ether groups.

Importantly, the hydrocarbyl groups of the ligands have a sufficient number of carbon atoms to render the compounds soluble or dispersible in oil. The compounds' oil solubility or dispersibility may be influenced by the number of carbon atoms in the ligands. Preferably the ligands have a sufficient number of carbon atoms to render the compound soluble or dispersible in oil. The total number of carbon atoms present among all of the hydrocarbyl groups of the compounds' ligands typically will be at least 21, e.g., 21 to 800, such as at least 25, at least 30 or at least 35. For example, the number of carbon atoms in each alkyl group will generally range between 1 to 100, preferably 1 to 40, and more preferably between 3 and 20.

The $Mo_3S_xL_y$ reaction product is produced by reacting two to less than three preferably from 2 to 2.1, most preferably 2, molar equivalents of a tetrahydrocarbyl thiuram disulfide and one molar equivalent of a compound containing the $[Mo_3S_{13}]^{2-}$ ion, such as $(NH_4)_2Mo_3S_{13} \cdot nH_2O$ wherein n is 0–2 and includes non-integer values. The reaction is typically carried out at elevated temperature, typically 60° C. to 150° C. The reaction may be carried out in an inert atmosphere such as argon or nitrogen, it may also be carried out in the presence of an oxidizing source such as air, hydrogen peroxide or oxygen. The reaction may be carried out in the presence of a sulfur-abstracing agent such as triphenyl phosphine, a cyanide or a sulfite.

$Mo_3S_x(L)_y$, wherein L is dihydrocarbyldithiocarbamate, x is 4 to 10 and y is 4 is currently synthesized as disclosed in copending, commonly assigned application Ser. No. 766, 831 filed Dec. 13, 1996 using three equivalents of thiuram disulfide to one equivalent of $(NH_4)_2Mo_3S_{13} \cdot 2H_2O$. This reaction, undesirably results in the formation of two molar equivalents of a $(NH_4)L_y$ byproduct that must be removed or further treated in order to reduce its corrosivity to seals and copper. Beneficially, Applicants' invention decreases the amount of ligand source that is required as a starting material and produces an absence or an essential absence of such undesired byproduct in the product. The resulting $Mo_3S_xL_y$ in the reaction mixture may be isolated.

The reaction product is useful as a multifunctional lube additive having enhanced antifriction, antiwear and antioxidant properties and may be used to enhance antifriction, antiwear and antioxidancy properties of an oil of lubricating viscosity by adding the reaction product thereto.

The invention may be demonstrated with reference to the following examples:

GENERAL

As used herein "coco" is an alkyl chain or mixture of chains of varying even numbers of carbon atoms, typically from $C_8$ to $C_{18}$.

EXAMPLE 1

Synthesis of "$Mo_3S_7(dtc)_4$" from two equivalents of thiuram disulfide ("TDS") under an inert atmosphere was carried out by placing $(NH_4)_2Mo_3S_{13} \cdot 2H_2O$ (7.76 g, 10 mmol) and tetracocothiuram disulfide (19.5 g, 20 mmol) in a flask which was evacuated and filled three times with Ar. Oxygen free toluene (50 mL) and methanol (50 mL) were added to the flask and the solvents were degassed. The solution was refluxed vigorously for eight hours. Workup was as follows: The solvents were pumped off. The product was dissolved in heptane and filtered. The heptane was pumped off to yield approximately 25 g of $Mo_3S_7(dtc)_4$.

EXAMPLE 2

Synthesis of "$Mo_3S_7(dtc)_4$ with air/$O_2$ purge was carried out by placing $(NH_4)_2Mo_3S_{13} \cdot 2H_2O$ (7.76 g, 10 mmol) and tetracocothiuram disulfide (19.5 g, 20 mmol) in a flask. Toluene (50 mL) and methanol (50 mL) were added to the flask. The solution was refluxed vigorously for eight hours while air was purged through the solution. Workup was as follows: The solvents were pumped off. The product was dissolved in heptane and filtered. The heptane was pumped off to yield approximately 25 g of $Mo_3S_7(dtc)_4$.

EXAMPLE 4

Three molybdenum containing oils were tested for friction retention properties by comparing the High Frequency Reciprocating Rig (HFRR) performance of the fresh oils with that of the aged oils. The oils were aged by treatment with 1% $NO_2$ in air at 60 ml/minute and at 150° C. for 24 hours. The friction properties were then recorded at 140° C. and compared with the results from the fresh oils. Three oils were compared through this method each containing equivalent amounts (500 ppm) of molybdenum through three different molybdenum sources. The molybdenum components were MV822, a commercial dinuclear component (available from Vanderbilt Chemical Company); $Mo_3S_7dtc_4$ synthesized via the three equivalents TDS route; and $Mo_3S_7dtc_4$ synthesized via the two equivalents TDS route. The results of these tests are shown in Table 1. Both the trinuclear molybdenum containing oils showed improved friction retention properties over the oil containing MV822. It is also evident that the trinuclear molybdenum compounds synthesized via both the two equivalent and the three equivalent routes give comparable performance results.

TABLE 1

| Molybdenum compound (@ 500 ppm) | MV822 | 3 TDS $Mo_3S_7dtc_4$ | 2 TDS $Mo_3S_7dtc_4$ |
| --- | --- | --- | --- |
| coefficient of friction for fresh oil | 0.096 | 0.086 | 0.095 |
| coefficient of friction for used oil | 0.158 | 0.079 | 0.084 |

What is claimed is:

1. A method of making an oil-soluble or oil-dispersible trinuclear molybdenum-sulfur compound, comprising: reacting two to less than three equivalents of a tetrahydrocarbyl thiuram disulfide and one equivalent of a compound containing the $[Mo_3S_{13}]^{2-}$ ion to produce a trinuclear molybdenum compound of the formula $Mo_3S_x(L)_4$ wherein x is from 4 to 10 and L is dihydrocarbyl-dithiocarbamate.

2. The method of claim 1 wherein two equivalents of the tetrahydrocarbyl thiuram disulfide are reacted.

3. The method of claim 1 wherein the reaction is carried out in an inert atmosphere.

4. The method of claim 1 wherein the reaction is carried out in the presence of an oxidizing source.

5. The method of claim 1 wherein x is 4 or 7.

6. The method of claim 1 wherein the hydrocarbyl groups are alkyl groups having 3 to 20 carbon atoms.

7. A trinuclear molybdenum sulfur compound produced by the method of claim 1.

8. A trinuclear molybdenum-sulfur compound produced by the method of claim 2.

9. A lubricating oil composition comprising a major amount of an oil of lubricating viscosity and a minor amount of the compound of claim 8.

10. A lubricating oil composition, comprising a major amount of an oil of lubricating viscosity and a minor amount of the compound of claim 7.

11. A method of enhancing the antifriction, antiwear and antioxidancy properties of an oil of lubricating viscosity, comprising adding to the lubricating oil an antifriction, antiwear and antioxidancy enhancing amount of the reaction product of from two to less than three equivalents of a tetrahydrocarbyl thiuram disulfide and one equivalent of a compound containing the $[Mo_3S_{13}]^{2-}$ ion to produce a trinuclear molybdenum compound of the formula $Mo_3S_x(L_4)$ wherein x is from 4 to 10 and L is dihydrocarbyl dithiocarbamate.

* * * * *